United States Patent [19]

Tsuda et al.

[11] Patent Number: 5,763,718
[45] Date of Patent: Jun. 9, 1998

[54] PROCESS FOR PRODUCING OCTADIENES

[75] Inventors: Tomoyasu Tsuda; Noriaki Yoshimura, both of Okayama-ken, Japan

[73] Assignee: Kuraray Co., Ltd., Kurashiki, Japan

[21] Appl. No.: 534,313

[22] Filed: Sep. 27, 1995

[30] Foreign Application Priority Data

Sep. 28, 1994 [JP] Japan ............................. 6-233072
Sep. 1, 1995 [JP] Japan ............................. 6-225125

[51] Int. Cl.$^6$ .............................. C07C 2/46; C07C 13/26
[52] U.S. Cl. ........................... 585/370; 585/368; 585/367
[58] Field of Search ............................ 585/366, 367, 585/368, 369, 370

[56] References Cited

U.S. PATENT DOCUMENTS 4,554,375  11/1985  Lin et al. ........................... 560/244

FOREIGN PATENT DOCUMENTS

A-0 004 410  10/1979  European Pat. Off. .

OTHER PUBLICATIONS

Musco, *Journal of the Chemical Society, Perkin Transactions I*, pp. 693–698 (1980) no month.

*Primary Examiner*—Glenn Caldarola
*Assistant Examiner*—Alexander G. Ghyka
*Attorney, Agent, or Firm*—Oblon, Spivak, McClelland, Maier & Neustadt, P.C.

[57] ABSTRACT

A process for producing octadienes comprises, on synthesis of octadienes by reacting butadiene with formic acid in the presence of a palladium catalyst, controlling the reaction pressure at not more than the vapor pressure of butadiene at the reaction temperature employed, thereby suppressing formation of byproducts which would accumulate in a catalyst-containing layer and minimizing the decrease of reaction rate and selectivity which would occur by such accumulation.

5 Claims, No Drawings

PROCESS FOR PRODUCING OCTADIENES

BACKGROUND OF THE INVENTION

1. Field of the Invention

The present invention relates to a process for producing octadienes by reacting butadiene with formic acid.

Among the octadienes obtained by the process of the present invention, 1,7-octadiene is important as a crosslinking agent on production of polyolefins and as an intermediate for synthesizing sebacic acid, C10 diols and C10 diamines which are useful as starting materials for polyesters, polyamides and alkyd resins as well as for plasticizers.

2. Description of the Prior Art

The reaction of synthesizing octadienes by reacting butadiene with formic acid in the presence of a palladium catalyst is known. Japanese Patent Application Laid-open Nos. 29703/1973, 130505/1979, 19275/1980 and 130504/1979 and Journal of Molecular Catalysis, 15, 377–381 (1982) describe use of, on conducting the formation reaction of octadienes, catalysts modified by triarylphosphines, trialkylphosphines or like organic phosphorus compounds. Japanese Patent Application Laid-open No. 81819/1980 describes use of a catalyst containing as a tertiary organic phosphorus ligand a tertiary organic phosphinite, a tertiary organic phosphonite or mixtures of the foregoing; and Japanese Patent Application Laid-open No. 81820/1980 describes use of a catalyst containing as a tertiary organic phosphorous ligand a mixture of any two compounds selected from the group consisting of phosphine, phosphite, phosphinite and phosphonite. The use of these modified catalysts is very effective in improving the selectivity on the formation of octadienes. However, known processes including those described in the above prior art, with which the catalyst used forms a homogeneous mixture with the starting material olefin or the product, require the step of distilling the reaction mixture to separate the catalyst and the product. Then, the catalyst, having poor thermal stability, is heated. As a result, the catalyst will become entirely or partly degraded, or high boiling polymers forming as byproducts during the reaction will, in the course of circulating the catalyst for reuse, accumulate in the reaction zone and decrease the activity of the catalyst.

In order to solve the above problems encountered on commercial production, Japanese Patent Publication No. 17567/1987 discloses a process which comprises effecting the reaction, while maintaining the water content in the reaction mixture at 5% by weight or below, in a polar solvent such as sulfolane and/or the formate of a tertiary amine and in the presence of a hydrophilic phosphine; after completion of the reaction, separating the reaction mixture after as necessary adding formic acid thereto into an octadiene-containing layer and a catalyst-containing layer in the presence or absence of an extractant; and circulating the catalyst-containing layer to the production step of octadienes. As a result of a detailed study on the above process for producing octadienes from butadiene, the present inventors have found that with this process a considerable amount of lactones form as byproducts with formation of octadienes. Formation of lactones on reaction of butadiene with carbon dioxide at high pressure in the presence of a palladium catalyst is known [see, for example, Journal of Chemical Society, Perkin Transaction I, 693–698 (1980)]. However, formation of lactones with carbon dioxide, even at low pressure, formed by reaction of formic acid, as is the case with this reaction zone, has been never realized. It has thus been found that: with the process described in Japanese Patent Publication No. 12567/1987, byproduction of lactones, which will be distributed into the catalyst-containing layer and act as catalyst poison, causes the serious problem of decreasing the yield of octadienes, thereby rendering it impossible to continue the operation over a long period of time.

Palladium catalysts are known to be very expensive noble metal catalysts. In conducting mass-production of low-cost octadienes on a commercial scale, it is therefore very important to maintain over a long period of time the catalytic activity of the palladium catalyst used.

SUMMARY OF THE INVENTION

Accordingly, an object of the present invention is to provide a process for producing octadienes, which can, on production of octadienes by reacting butadiene with formic acid in the presence of a palladium catalyst, suppress the formation of byproducts that would accumulate in the catalyst-containing layer, and thus avoid a decrease in the reaction rate and selectivity, thereby being operatable over a long period of time under stable conditions.

According to the present invention, the above object can be achieved by providing a process for producing octadienes which comprises, on synthesis of octadienes by reacting butadiene with formic acid in the presence of a palladium catalyst, controlling the reaction pressure at not more than the vapor pressure of butadiene at the reaction temperature employed.

The above object can also be achieved by providing a process for producing octadienes which comprises the steps of:

(i) on synthesis of octadienes by reacting butadiene with formic acid in an aprotic polar solvent having a dielectric constant of 39 to 100 in the presence of the formate of a tertiary amine, a palladium catalyst and an organic phosphorus compound represented by the following general formula (I)

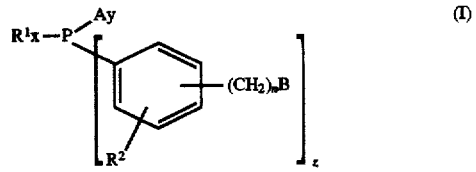

wherein $R^1$ represents a hydrocarbon group which may be substituted; $R^2$ represents a hydrogen atom, an alkyl group, a nitro group, a cyano group, an alkoxyl group or a halogen atom, n represents 0 or an integer of 1; x represents 0 or an integer of 1 or 2; y and z each represents 0 or an integer of 1, 2 or 3 (provided that y and z are not concurrently equal to 0 and that x+y+z=3); and A represents —$R^3$—COOM, —$R^3NR^4R^5$ or the carbonate, bicarbonate or formate of —$R^3$—$NR^4R^5$ and B represents —$SO_3M$, —COOM, —$NR^4R^5$ or the carbonate, bicarbonate or formate of —$NR^4R^5$ wherein $R^3$ represents an alkylene group which may be substituted, $R^4$ and $R^5$ each represents an alkyl group or $R^4$ and $R^5$ bound together represent an alkylene group and M represents an alkali metal, and/or another organic phosphorus compound represented by the following general formula (II)

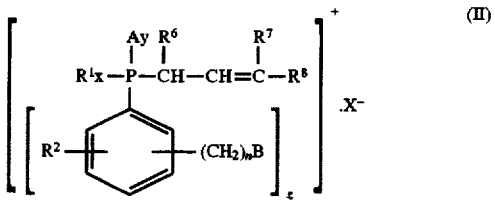

wherein $R^1$, $R^2$, n, x, y, z, A and B are as defined above; $R^6$, $R^7$ and $R^8$ each represents a hydrogen atom or a hydrocarbon group which may be substituted and X represents a hydroxyl group, a hydroxycarbonyloxy group, an alkylcarbonyloxy group or a formyloxy group; controlling the reaction pressure at not more than the vapor pressure of butadiene at the reaction temperature employed;

(ii) transferring at least part of the reaction mixture obtained in step (i) to a vessel for allowing said at least part of the reaction mixture to stand still (hereinafter referred to as "standing vessel") and separating it into an octadiene-containing layer and a catalyst-containing layer; and (iii) circulating at least part of the catalyst-containing layer obtained in step (ii) to step (i) for octadiene synthesis.

DETAILED DESCRIPTION OF THE PREFERRED EMBODIMENTS

In step (i), the concrete means for controlling the reaction pressure at not more than the vapor pressure of butadiene at the reaction temperature comprises equipping the reactor with a pressure control valve, thereby controlling the pressure at not more than the vapor pressure of butadiene at the reaction temperature, and discharging at least part of the carbon dioxide generating during the reaction. There is a known relationship obtained from the following Antoine equation, between the temperature (t(°C.)) and the saturated vapor pressure (P(mmHg)) of conventional organic compounds (Kagaku Benran, 3rd Revision, Kiso-hen II, 111 (1984), issued by Maruzen):

$$\log [P(mmHg)] = A - B/\{C + \{t(°C.)\}\}.$$

With butadiene, having A=6.8500, B=930.55 and C=238.85, the saturated vapor pressures at different temperatures nearly become: 30° C.-3.3 atom, 47° C.-5.0 atm, 60° C.-7.4 atom, 70° C.-9.3 atom, 90° C.-14.0 atm and 114° C.-20.0 atm.

If in step (i) the reaction pressure exceeds the vapor pressure of butadiene at the reaction temperature, the content in the reaction zone of carbon dioxide generating by reaction will increase, which generally causes byproduction of lactones. Although there is no particular lower limit of the reaction pressure as long as it is kept at not more than the vapor pressure of butadiene, a low pressure level of about atmospheric pressure causes butadiene to be discharged off from the reaction zone, so that it becomes difficult to operate stably while keeping the inside of the reaction zone under constant conditions.

Commercial available butadiene of polymerization grade or chemical reaction grade or hydrocarbon mixtures generally called C4-fraction in petrochemical industry can be used for the process of the present invention. However, polymerization grade or chemical reaction grade is preferred in view of reaction rate and ease of recovery of unreacted butadiene. In the present invention, although there is no particular limitation to the concentration of butadiene, it is desirable to maintain the butadiene concentration at at least 0.6 mole per liter of the reaction mixture in view of reaction rate and the octadiene concentration in the reaction mixture. The upper limit of the butadiene concentration is not specifically restricted, but in general the concentration is desirably not more than 5 mole/l from the viewpoint of the amount to recover.

The production of octadienes according to the present invention can be conducted in the presence of an aprotic organic solvent. In particular, use of an aprotic polar solvent having a dielectric constant of 39 to 100 is desirable for the purpose of achieving a high reaction rate. Examples of such a solvent are acetonitrile, sulfolane, methylsulfolane, dimethyl sulfoxide and ethylene carbonate. Among these, sulfolane is more preferred in consideration of reaction rate, selectivity of reaction, stability, low level of amounts eluted of various components and high separability from octadiene.

In the present invention, it is possible to use either anhydrous formic acid or water-containing formic acid. Anhydrous formic acid is preferred for commercial production, since use of water-containing formic acid with circulation of catalyst leads to accumulation of water in the reaction zone. Use of formic acid in the form of the salt of a monodentate tertiary amine having a dissociation constant (pKa) of at least 7 achieves a high reaction rate. Anhydrous mixtures of formic acid and a tertiary amine can be easily obtained by mixing an aqueous formic acid, which is readily available commercially, with the tertiary amine and then removing water by azeotropic distillation with the tertiary amine. To this end, it is desirable to use such a monodentate tertiary amine as can undergo azeotropic distillation with water at a temperature lower than the boiling point (100.8° C.) of formic acid. The monodentate tertiary amine may be used in any amount but is generally used in an equimolar amount based on formic acid. It is more desirable to use as formic acid an azeotropic mixture of a monodentate tertiary amine and formic acid. Concrete examples of monodentate tertiary amines usable in the present invention are tri(lower alkyl)amines, e.g. trimethylamine, triethylamine, tri-n-propylamine and tri-n-butylamine, and cyclic tertiary amines, e.g. N-methylpiperidine and N-methylmorpholine. Among these, use of triethylamine is particularly preferred in consideration of availability, ease of handling, boiling point, boiling point of anhydrous azeotropic mixture with formic acid, solubility and price. The formic acid-triethylamine azeotropic mixture can be readily obtained by mixing a commercially available 76% by weight aqueous formic acid solution, which is an azeotropic mixture of water and formic acid, with triethylamine, then removing the water by azeotropic distillation with triethylamine and, thereafter, subjecting the remaining mixture to vacuum distillation. The anhydrous azeotropic mixture has a composition of formic acid:triethylamine of about 5:2 (molar ratio).

In the present invention, the concentration of the formate of a monodentate tertiary amine is selected in view of the solubility in the reaction mixture of butadiene present therein. It is desirable, from the viewpoint of reaction rate, that the concentration of the formate of the monodentate tertiary amine be not more than 2 moles, more preferably not more than 1.6 moles, per liter of the reaction mixture. Although there are no restrictions in a strict sense with respect to the lower limit of the concentration of the formate of the monodentate tertiary amine in the reaction mixture, it is desirable, for the purpose of conducting continuous operation stably over a long period of time, to maintain the concentration at at least 0.3 mole per liter of the reaction mixture. If the concentration exceeds 2 mole/l, the solubility of butadiene in the reaction mixture will decrease, which sometimes causes a decrease in the reaction rate.

In the present invention, the palladium catalyst to be present in the reaction zone is an active species derived from palladium or palladium compounds. Any palladium compound may be used for forming the palladium catalyst with no specific restrictions and, for example, those having been proposed for use in the synthesis of octadienes are usable for this purpose. Concrete examples of these palladium compounds are palladium acetylacetonate, π-allyl-palladium acetate, π-allylpalladium chloride, palladium acetate, palladium carbonate, palladium nitrate, palladium chloride, sodium chloropalladate, bis(benzonitrile)palladium chloride, bis(triphenylphosphine)palladium chloride, bis(triphenylphosphine)palladium acetate, bis(1,5-cyclooctadiene)palladium and bis-π-allyl palladium. The true palladium catalysts in the synthesis of octadienes are low-valent palladium complexes. With use of a divalent palladium compound, it is therefore possible either to reduce the compound with butadiene or the monodentate phosphine present in the reaction mixture, into a palladium catalyst, or reacting the compound in the same reaction zone or a separate reaction vessel with a reducing agent to form a palladium catalyst, which is then used. Examples of reducing agents usable for this purpose are sodium borohydride, zinc dust, magnesium and hydrazine. Although there is no specific limitation to the amount of the palladium catalyst to be present in the reaction zone, it is used, for commercial production, in such an amount as to make the concentration 0.1 to 50 mg-atom, more preferably 0.5 to 5 mg-atom, per liter of the reaction mixture.

In the present invention, the reaction can be effected in the presence of any known organic phosphorus compound. In particular, use of a hydrophilic monodentate tertiary phosphine represented by general formula (I) and/or phosphonium salt represented by general formula (II) dissolvable in the solvent under reaction conditions, as the organic phosphorus compound to be present in the reaction zone, makes it possible to employ the continuous process described in Japanese Patent Publication No. 17567/1987, thereby achieving a long-term use by circulation of the catalyst used.

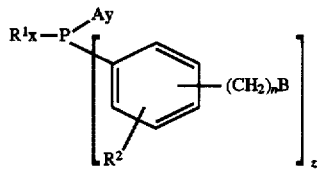

(I)

wherein $R^1$, $R^2$, n, x, y, z, A and B are as defined before.

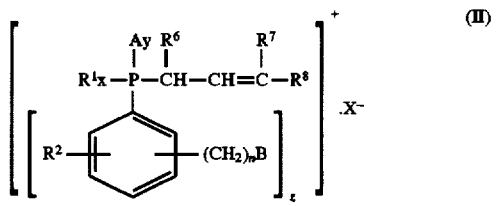

(II)

wherein $R^1$, $R^2$, $R^6$, $R^7$, $R^8$, n, x, y, z, A, B and X are as defined before.

As the hydrocarbon group represented by $R^1$ in general formulas (I) and (II), those having 1 to 8 carbon atoms are desirable. Concrete examples of these hydrocarbons are linear and branched aliphatic hydrocarbons, e.g. methyl, ethyl, n-propyl, isopropyl, n-butyl, t-butyl and n-octyl; alicyclic hydrocarbon groups, e.g. cyclohexyl and methylcyclohexyl; and aromatic hydrocarbons, e.g. phenyl, benzyl and tolyl. The aromatic hydrocarbons may be substituted with an alkoxyl group such as methoxy, a halogen atom such as chlorine atom, a cyano, a nitro or like groups.

With $-R^3-COOM$, $-R^3-NR^4R^5$ or the carbonate, bicarbonate or formate of $-R^3-NR^4R^5$ represented by A in general formulas (I) and (II), the alkylene group represented by $R^3$ is desirably one having 1 to 8 carbon atoms. Examples of the desirable alkylene groups are methylene, ethylene, propylene, butylene and octylene. These alkylene groups may be substituted by alkyl group. Examples of the alkyl group represented by $R^4$ or $R^5$ are methyl, ethyl and propyl. Examples of the alkylene group represented by $R^4$ and $R^5$ bound together are butylene and amylene.

With $-SO_3M$ and $-COOM$ which may be represented by B in general formulas (I) and (II), M represents an alkali metal. Preferred alkali metals represented by M are sodium, potassium and lithium. The monodentate phosphine with B in general formula (I) being $-SO_3M$ or $-COOM$ is generally used in the form of an alkali metal salt. It is, however, also possible to use, instead of the alkali metal salt, a free sulfonic acid, carboxylic acid or esters of the foregoing and react it, in the reaction zone or in a separate reaction vessel, with a salt, such as hydroxide, bicarbonate or carbonate, of an alkali metal, to form the alkali metal salt.

Among the monodentate phosphines represented by general formula (I), particularly preferred ones are diaryl and triaryl phosphines with, in general formula (I), the $R^1$ being an aromatic hydrocarbon group, the n being 0 or an integer of 1, the x being 0 or an integer of 1 or 2, the y being 0 or an integer of 1, the z being 0 or an integer of 1, 2 or 3 (provided that y and z are not concurrently equal to 0 and that x+y+z=3), the A being $-CH_2CH(CH_3)COOM$ and the B being $-SO_3M$, $-COOM$, $-NR^4R^5$ or the carbonate, bicarbonate or formate of $-NR^4R^5$. Concrete examples of these phosphines are as follows.

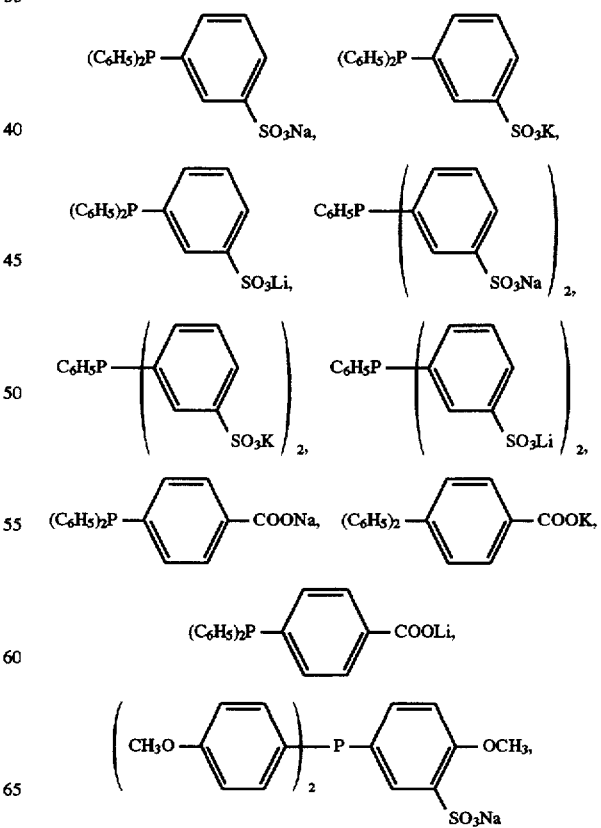

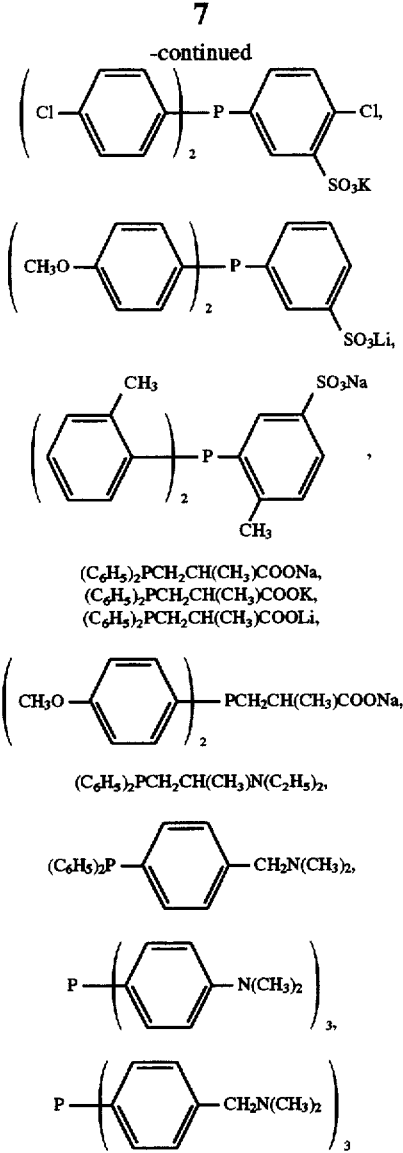

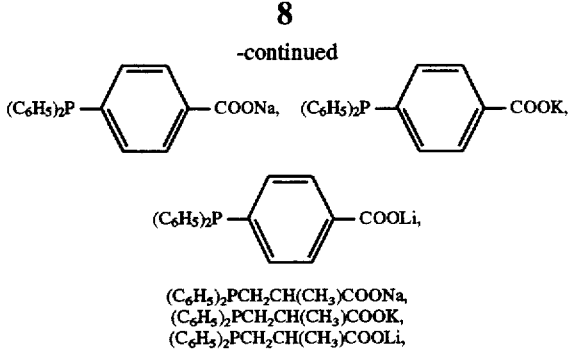

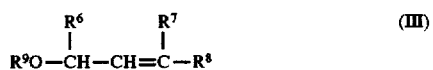

$(C_6H_5)_2PCH_2CH(CH_3)COONa,$
$(C_6H_5)_2PCH_2CH(CH_3)COOK,$
$(C_6H_5)_2PCH_2CH(CH_3)COOLi,$

Among the hydrophilic monodentate phosphines represented by general formula (I), those having amino group are generally added to the reaction zone as they are. However, since these phosphines will be present in the reaction zone in the form of the formate, it is also possible to prepare the formate of such amino group-containing phosphines separately and then add the formate to the reaction zone. These monodentate organic phosphorus compounds may be used singly or as admixtures of 2 or more.

The phosphonium salts represented by general formula (II) are synthesized by, for example, the process described in Japanese Patent Application Laid-open No. 85988/1989. These phosphonium salts may be synthesized beforehand and then used, or synthesized in the reaction zone prior to the reaction, by contacting the corresponding hydrophilic monodentate phosphines to an allyl compound represented by the general formula (III)

$$R^9O-\overset{R^6}{\underset{|}{C}H}-CH=\overset{R^7}{\underset{|}{C}}-R^8 \qquad (III)$$

wherein $R^6$, $R^7$ and $R^8$ are as defined before and $R^9$ is a hydrogen atom or an alkylcarbonyl group, in the presence of a palladium catalyst and then used as they are. Examples of the alkylcarbonyl group represented by $R^9$ in the general formula (III) are methylcarbonyl group and ethylcarbonyl group. Examples of the allyl compound are allyl alcohols, e.g. allyl alcohol, 2-methyl-2-propen-1-ol, 2-buten-1-ol, 2,5-hexadien-1-ol, 2,7-octadien-1-ol, 1,4-pentadien-3-ol, 1,7-octadien-3-ol and 2-octen-1-ol; and esters of an allyl alcohol and a carboxylic acid, e.g. allyl acetate, 2-methyl-2-propenyl acetate, 2,5-hexadienyl acetate, 2,7-octadienyl acetate, 1-vinyl-5-hexenyl acetate, 1-vinyl-2-propenyl propionate and 2-octenyl propionate. Where an allyl alcohol is used as the allyl compound represented by general formula (III) is used, the reaction is generally effected in the presence of water containing carbonate ion and/or bicarbonate ion, thereby yielding a phosphonium salt with the X in formula (II) being a hydroxyl group or a hydroxycarbonyloxy group. It is also possible to effect the reaction in the presence of formic acid, thereby obtaining a phosphonium salt with the X in formula (II) being a formyloxy group. Where the ester of an allyl alcohol and a carboxylic acid is used as the allyl compound represented by formula (III), it is possible to effect the reaction in the absence of water containing carbonate ion and/or bicarbonate ion, thereby forming a phosphonium salt with the X in formula (II) being an alkylcarbonyloxy group.

Any palladium compound usable in the present invention can also be permitted to be present in the reaction zone on the synthesis of the phosphonium salts. Formation reaction of the phosphonium salts represented by general formula (II) can be conducted in the presence of an organic solvent which is inactive to the reaction and can dissolve the hydrophilic monodentate phosphine represented by formula Among the above examples, particularly preferred hydrophilic phosphines are as follows.

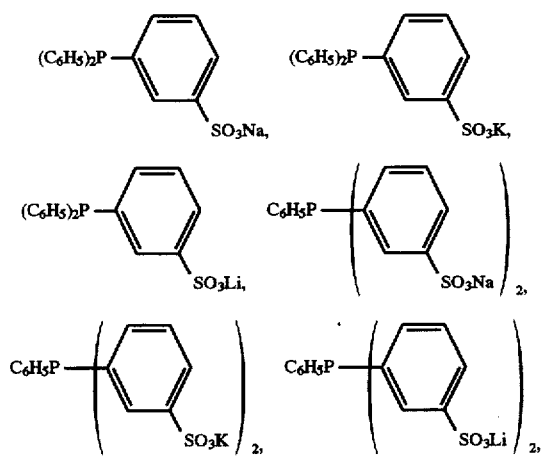

(I) and the allyl compound used. Any solvent usable for the reaction of the present invention can also be, as it is, used for this purpose.

Upon conducting, prior to the reaction, conversion reaction from phosphine to phosphonium salt in the reaction zone, with use of an allyl alcohol as the allyl compound, the water content of the reaction mixture is desirably set at not more than 5% in view of the reaction rate and selectivity on synthesis of octadienes. For the conversion reaction to phosphonium salt, use of the ester of an allyl alcohol and a carboxylic acid, which permits the conversion to be conducted in the absence of water in the reaction zone, is more preferred in view of the reaction rate and selectivity on synthesis of octadienes.

The hydrophilic monodentate organic phosphorus compound is used in an amount of generally at least 1 mole, preferably at least 6 moles, more preferably at least 10 moles per gram atom of palladium, in consideration of the level of reaction rate and selectivity to octadiene, long-period stabilization of the catalytic activity of the palladium catalyst, the effect of suppressing, in the succeeding step of separation by allowing the reaction mixture to stand still, elution of the palladium catalyst into the product layer containing octadiene and other factors. Although there is no upper limit in a strict sence of the amount of the monodentate organic phosphorus compound, it is generally used in an amount of not more than 150 moles, preferably not more than 80 moles, per gram atom of palladium.

The reaction temperature in step (i) is, differing depending on the reaction pressure though, generally in a range of 20° to 110° C. and preferably in a range of 40° to 90° C. in view of reaction rate and ease of reaction operation. The reaction can be conducted in any known gas-liquid-contact reaction vessel such as stirred tank reactor or bubbled column.

In the process of the present invention, it is possible to separate the reaction mixture containing the formed octadienes by subjecting it to a short-time distillation at a relatively low temperature of not more than 80° C. However, this distillation separation tends to cause deactivation of the palladium catalyst due to accumulation of high boiling substances originating from dienes and olefins and degradation or deactivation by metallization of the catalyst due to the heating. As a result, it becomes difficult to continue the operation stably over a long period of time. In order to separate the reaction mixture into octadiene and catalyst in the present invention, it is therefore desirable to employ either of the following two methods. The one comprises, after as necessary cooling the reaction mixture, allowing it to stand, which causes the reaction mixture to separate into an octadiene-containing layer (upper layer) and a catalyst-containing polar solvent layer (lower layer), and then simply separating the upper and lower layers. The other comprises, after as necessary cooling the reaction mixture, adding an extractant to the mixture to extract octadienes therewith and then separating the resulting mixture into upper and lower layers. The octadiene-containing layer thus obtained can then be subjected to the usual separation procedure such as distillation, to separate the octadienes.

On the above extraction, octadienes can be more advantageously separated from the reaction mixture by permitting an extractant selected from saturated aliphatic hydrocarbons, unsaturated hydrocarbons or alicyclic hydrocarbons to be present in combination in an appropriate amount. Preferred extractants for this purpose are those saturated hydrocarbons, unsaturated hydrocarbons and alicyclic hydrocarbons having a lower boiling point than octadienes. Examples of such extractants are saturated hydrocarbons, e.g. n-butane, n-pentane, n-hexane, hexanes and n-heptane; unsaturated hydrocarbons, e.g. butene and isobutene and alicyclic hydrocarbons, e.g. cyclohexane, cyclohexene and methylcyclohexane. There can be also used mixtures of butane, butene, isobutene and like hydrocarbons contained in C4 fraction as butadiene source. Among the above, n-hexane and hexanes are particularly preferred. These extractants may be used singly or in admixtures. Octadiene can also be used as extractant. These extractants may be used in any amount, but desirably in a ratio by weight ranging from about 1/10 to 10 based on the reaction mixture. As the extraction apparatus for using an extractant, a commercially available stirring type extraction column, RDC type extraction column, perforated plate column or the like is usable. However, for commercial practice of the process of the present invention, provision of a standing vessel sufficient for separating the reaction mixture into layers, with use of no extractant, is advantageous, since extraction apparatus and equipment required for feeding extractant and distillation recovery can then be omitted.

The lower layer containing catalyst obtained by the standing separation step can be circulated to the synthesis step of octadienes and re-used. As desired, part of the lower layer may be taken out and, after being subjected to catalyst activation treatment, circulated to the synthesis step of octadienes. By the procedure of the standing separation step, the products (1,7-octadiene, 1,6-octadiene, 1,3,7-octatriene, high boiling byproducts and others) are separated into a product layer containing extractant or no extractant. The product layer may sometimes contain unreacted butadiene, monodentate tertiary amine and trace amounts of reaction solvent, palladium catalyst, organic phosphorus compound and other components. The product layer obtained by the standing separation step may be washed with water to extract water-soluble components contained in the product layer, such as the solvent, palladium catalyst and the like used for the reaction. Then, the obtained water containing the water-soluble components can be subjected to distillation to remove the water and the residue can be used for the synthesis of octadienes.

Other features of the invention will become apparent in the course of the following detailed descriptions of exemplary embodiments which are given for illustration of the invention and are not intended to be limiting thereof.

EXAMPLE 1

A continuous reaction experiment was conducted with the apparatuses described below, to study the reaction results at a steady state.

Reaction apparatus:

a glass autoclave equipped with a temperature controller, a butadiene metering feed pump, a feed pump for anhydrous azeotropic mixture of formic acid and triethylamine (molar ratio between formic acid and triethylamine is 5:2), a feed pump for additional sulfolane liquid and a pressure control valve. The reaction pressure is always maintained at a set value by pressure control valve. The reaction mixture is pumped, via a pressure reducing valve, to a standing separation apparatus.

Standing separation apparatus:

a glass autoclave equipped with a thermometer. The product layer is fed by feed pump to a distillation apparatus at a constant rate, and the lower catalyst-containing layer is fed to the reaction vessel by a catalyst feed pump at a constant rate.

Distillation apparatuses:

a pressure distillation apparatus for recovering by distillation of butadiene from the product layer and an atmospheric distillation apparatus for recovering by distillation triethylamine from the obtained residue. The recovered butadiene is returned to a butadiene tank.

Reaction conditions and results:

The composition of the reaction mixture in the reaction apparatus at a steady state was maintained at 50.1% by weight of sulfolane, 1.0 mole/l of triethylamine formate, 2.1 mg-atom/l of a palladium catalyst (prepared from palladium acetate), 80.4 mg-atom/l (in terms of phosphorus atom) of an organic phosphorus compound (a phosphonium salt synthesized in the zone from lithium diphenylphosphinobenzene-m-sulfonate and octadienyl acetate was used), 2.8 mole/l of butadiene, 1.07 mole/l of octadiene and 0.41 mole/l of triethylamine; and operation was run under the conditions of a reaction temperature of 70° C. (saturated vapor pressure of butadiene at 70° C. is about 9.3 kg/cm$^2$), a reaction pressure of 7.5 kg/cm$^2$ and a residence time of reaction mixture of 0.77 hour. The reaction mixture was separated at 20° C. in the standing separation apparatus.

The product layer and the reaction solvent were analyzed by gas chromatography, the amount of formate by titration with an aqueous sodium hydroxide solution, the palladium component by atomic absorption analysis and the phosphorus component by calorimetric determination. As a result, it was found that the octadiene concentration in the product layer was 2.7 mole/l, the selectivity based on formic acid nearly 100% and that based on the reacted butadiene 95.5%. The ratio between the amount formed of 1,7-octadiene and 1,6-octadiene in octadienes was 89/11. These results show that the rate of formation of octadienes was 1.19 mole/l·hr. The amounts of solvent, catalyst and others eluted in the product layer were, as converted per kg of 1,7-octadiene, not more than 0.6 mg of palladium (as atom), 4 mg of phosphorus (as atom), 107 g of sulfolane and 367 g of triethylamine. Continuous operation was run for 21 days, while there were being added to the reaction apparatus anhydrous azeotropic mixture of formic acid-triethylamine containing formic acid in an amount corresponding to that of formic acid consumed by the reaction, palladium acetate and the phosphonium salt prepared from lithium diphenylphosphino-benzene-m-sulfonate and octadienyl acetate in amounts corresponding to the palladium component and phosphorus component having eluted and sulfolane in the same amount as that eluted. The operation was stable with constant reaction results. Throughout the operating period, no formation of lactones was observed at all.

EXAMPLE 2

Example 1 was repeated except that the operation period was prolonged to 90 days. Again, the operation was stable with similar reaction results to those in Example 1. Throughout the operating period, no formation of lactones was observed at all.

EXAMPLE 3

Example 1 was repeated with the same reaction equipment as used in Example 1, except that the composition of the reaction mixture in the reaction apparatus was maintained at 48.4% by weight of sulfolane, 1.23 mole/l of triethylamine formate, 2.1 mg-atom/l of a palladium catalyst (prepared from palladium acetate), 80.4 mg-atom/l (in terms of phosphorus atom) of an organic phosphorus compound (a phosphonium salt synthesized in the zone from lithium diphenylphosphinobenzene-m-sulfonate and octadienyl acetate was used), 3.1 mole/l of butadiene, 0.70 mole/l of octadiene and 0.28 mole/l of triethylamine and that the operation was run under the conditions of a reaction temperature of 60° C. (saturated vapor pressure of butadiene at 60° C. is about 7.4 kg/cm$^2$), a reaction pressure of 6.1 kg/cm$^2$ and a residence time of reaction mixture of 0.83 hour. It was found that the octadiene concentration in the product layer was 2.2 mole/l, the selectivity based on formic acid nearly 100% and that based on the reacted butadiene 95.6%. The ratio between the amount formed of 1,7-octadiene and 1,6-octadiene in octadienes was 89/11. These results show that the rate of formation of octadienes was 0.70 mole/l·hr. The amounts of solvent, catalyst and others eluted in the product layer were, as converted per kg of 1,7-octadiene, not more than 0.6 mg of palladium (as atom), 4 mg of phosphorus (as atom), 144 g of sulfolane and 367 g of triethylamine. Continuous operation was run for 10 days, while there were being added to the reaction apparatus anhydrous azeotropic mixture of formic acid-triethylamine containing formic acid in an amount corresponding to that of formic acid consumed by the reaction, palladium acetate and the phosphonium salt prepared from lithium diphenylphosphinobenzene-m-sulfonate and octadienyl acetate in amounts corresponding to the palladium component and phosphorus component having eluted and sulfolane in the same amount as that eluted. The operation was stable with constant reaction results. Throughout the operating period, no formation of lactones was observed at all.

COMPARATIVE EXAMPLE

After completion of the steady operation of Example 3, operation was further run for 10 days in the same manner as in Example 3 except that the reaction pressure was changed to 10 kg/cm$^2$ during the reaction. After the 10 days, the octadiene concentration in the product layer was found to be 2.05 mole/l, the selectivity based on formic acid nearly 100% and that based on the reacted butadiene 95.6%. The ratio between the amount formed of 1,7-octadiene and 1,6-octadiene in octadienes was 89/11. These results show that the rate of formation of octadienes was 0.65 mole/l·hr. During the 10 days operation, byproduction of lactones together with their accumulation in the catalyst-containing layer (sulfolane layer) was observed. Analysis of the sulfolane layer after completion of the reaction revealed the presence of lactones in an amount of 0.05 mole/l, which clearly shows that the decrease in the rate of formation of octadienes was due to catalyst poisoning caused by byproduction and accumulation of lactones. The amounts of solvent, catalyst and others eluted in the product layer were, as converted per kg of 1,7-octadiene, not more than 0.6 mg of palladium (as atom), 4 mg of phosphorus (as atom), 144 g of sulfolane and 367 g of triethylamine.

Obviously, numerous modifications and variations of the present invention are possible in light of the above teachings. It is therefore to be understood that within the scope of appended claims, the invention may be practiced otherwise than as specifically described herein.

What is claimed is:

1. A process for producing octadienes which comprises, on synthesis of octadienes and generation of carbon dioxide by reacting butadiene with formic acid in the presence of a palladium catalyst, controlling the reaction pressure at not more than the vapor pressure of butadiene at the reaction temperature employed by discharging at least part of the carbon dioxide generated.

2. A process for producing octadienes which comprises the steps of:

(i) on synthesis of octadienes and generation of carbon dioxide by reacting butadiene with formic acid in an aprotic polar solvent having a dielectric constant of 39 to 100 in the presence of the formate of a tertiary amine, a palladium catalyst and an organic phosphorus compound represented by the following general formula (I)

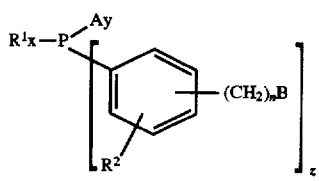

(I)

wherein $R^1$ represents a hydrocarbon group which may be substituted; $R^2$ represents a hydrogen atom, an alkyl group, a nitro group, a cyano group, an alkoxyl group or a halogen atom; n represents 0 or an integer of 1; x represents 0 or an integer of 1 or 2; y and z each represents 0 or an integer of 1, 2 or 3 (provided that y and z are not concurrently equal to 0 and that x+y+z= 3); and A represents —$R^3$—COOM, —$R^3NR^4R^5$ or the carbonate, bicarbonate or formate of —$R^3$—$NR^4R^5$ and B represents —$SO_3M$, —COOM, —$NR^4R^5$ or the carbonate, bicarbonate or formate of —$NR^4R^5$ wherein $R^3$ represents an alkylene group which may be substituted, $R^4$ and $R^5$ each represents an alkyl group or $R^4$ and $R^5$ bound together represent an alkylene group and M represents an alkali metal, and/or another organic phosphorus compound represented by the following general formula (II)

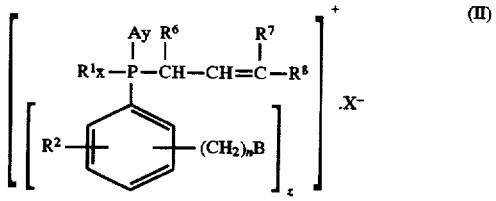

(II)

wherein $R^1$, $R^2$, n, x, y, z, A and B are as defined above; $R^6$, $R^7$ and $R^8$ each represents a hydrogen atom or a hydrocarbon group which may be substituted and X represents a hydroxyl group, a hydroxycarbonyloxy group, an alkylcarbonyloxy group or a formyloxy group; controlling the reaction pressure at not more than the vapor pressure of butadiene at the reaction temperature employed by discharging at least part of the carbon dioxide generated;

(ii) transferring at least part of the reaction mixture obtained in step (i) to a vessel for allowing said at least part of the reaction mixture to stand still and separating it into an octadiene-containing layer and a catalyst-containing layer; and (iii) circulating at least part of the catalyst-containing layer obtained in step (ii) to step (i) for octadiene synthesis.

3. The process according to either claim 1 or claim 2, wherein anhydrous formic acid is used as the formic acid to be reacted with butadiene.

4. The process according to either claim 1 or claim 2, wherein an anhydrous mixture of a monodentate tertiary amine having a dissociation constant (pKa) of at least 7 and formic acid is used as the formic acid to be reacted with butadiene.

5. The process according to either claim 1 or claim 2, wherein anhydrous azeotropic mixture of a monodentate tertiary amine having a dissociation constant (pKa) of at least 7 and formic acid is used as the formic acid to be reacted with butadiene.

* * * * *